(12) United States Patent
Aladsani

(10) Patent No.: US 12,201,782 B1
(45) Date of Patent: Jan. 21, 2025

(54) SUPPORTIVE AUDIO LISTENING DEVICES

(71) Applicant: KING FAISAL UNIVERSITY, Al-Ahsa (SA)

(72) Inventor: Lamia Aladsani, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/434,651

(22) Filed: Feb. 6, 2024

(51) Int. Cl.
    *A61M 21/02* (2006.01)
    *A61M 21/00* (2006.01)

(52) U.S. Cl.
    CPC ..... *A61M 21/02* (2013.01); *A61M 2021/0005* (2013.01)

(58) Field of Classification Search
    None
    See application file for complete search history.

(56) References Cited

U.S. PATENT DOCUMENTS

| | | | |
|---|---|---|---|
| 5,807,114 A | 9/1998 | Hodges et al. | |
| 11,623,088 B2 | 4/2023 | Covalin et al. | |
| 2013/0090949 A1* | 4/2013 | Tibebu | G16H 20/70 705/3 |
| 2021/0151166 A1* | 5/2021 | Schmid | G16H 50/20 |
| 2024/0123180 A1* | 4/2024 | Stewart | A61M 21/02 |

FOREIGN PATENT DOCUMENTS

| | | |
|---|---|---|
| CN | 115054251 A | 9/2022 |
| JP | H11155955 A | 6/1999 |

OTHER PUBLICATIONS

Ovrcome, ovrcome.io, backdated to at least Feb. 2023 via the Wayback Machine (Year: 2023).*
Lee et al., "Effectiveness of different music-playing devices for reducing preoperative anxiety: a clinical control study", Int J Nurs Stud. Oct. 2011; 48(10): 1180-7, First available online on May 11, 2011.
Zawn Villnes, "VR therapy and its benefits for mental health", Medical News Today Website, First available online on Oct. 13, 2023.
Dr. Andrew Rosen, "Using Virtual Reality Therapy For Phobias", Center forAnxiety Disorders Website, First available online on Apr. 24, 2017.

* cited by examiner

*Primary Examiner* — Thaddeus B Cox
(74) *Attorney, Agent, or Firm* — Nath, Goldberg & Meyer; Joshua B. Goldberg

(57) ABSTRACT

A method of relieving fear in an individual, the method can include experiencing at least one fearing event by the individual; obtaining an audio listening device; accessing at least one fear-relieving file corresponding to the at least one fearing event; placing the audio listening device on the individual's ears; playing the at least one fear-relieving file; and listening to the at least one fear-relieving file to relieve the fear in the individual.

14 Claims, 2 Drawing Sheets

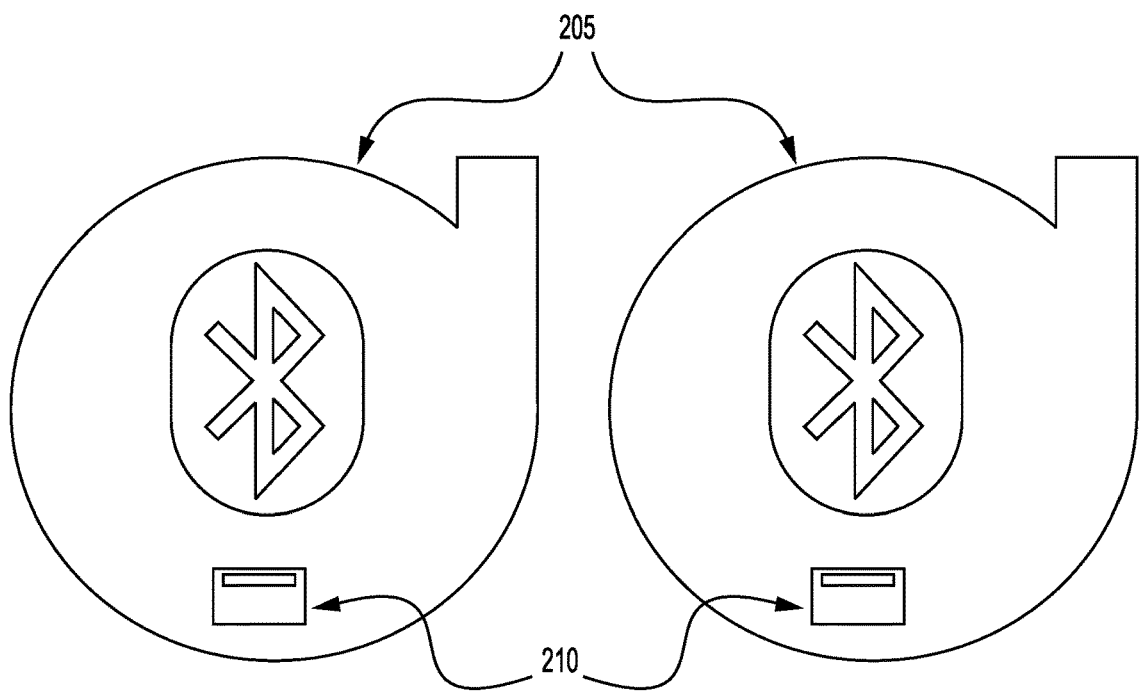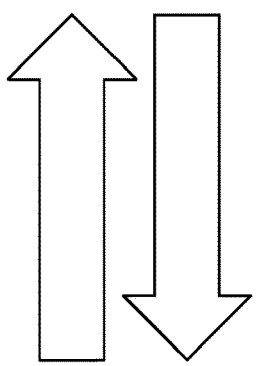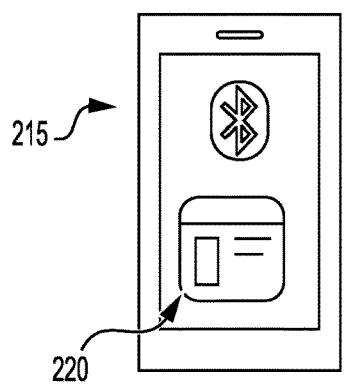
FIG. 2

SUPPORTIVE AUDIO LISTENING DEVICES

FIELD AND BACKGROUND

The disclosure of the present application relates to a method of relieving fear in an individual.

DESCRIPTION OF THE PRIOR ART

Phobia is an irrational fear associated with a certain stimulus like an object, an animal, an activity, a place, or a situation. It is a type of anxiety disorder. Exposure to the source of the fear triggers an immediate anxiety response. It causes a person to feel a sense of fear that is disproportionate to the actual danger that the source of the phobia presents.

Some common phobias are acrophobia, claustrophobia, megalophobia, and social phobia. People with acrophobia have an intense fear of heights such as being on a bridge, mountain, or a skyscraper. Individuals with claustrophobia have an intense fear of confined or enclosed spaces such as being in a tunnel, an elevator, an airplane, or MRI imaging machine. Megalophobia causes a person to experience an intense fear of large objects such as a large building, airplane, or a ship. Social phobia causes an individual to feel anxious or fearful in situations where they may be scrutinized, evaluated, or judged by others such as socializing with other people, speaking on the phone, or going to a party. In all these cases, the phobia may limit the person's daily activities and may cause severe anxiety, including depression, especially if the cause of the phobia is encountered regularly.

In light of the above, a need remains for helping an individual cope with the mentioned phobias by providing a method of relieving fear in the individual.

SUMMARY

The present subject matter relates to a method of relieving fear in an individual.

In one embodiment, the method of relieving fear in an individual includes experiencing at least one fearing event by the individual; obtaining an audio listening device; accessing at least one fear-relieving file corresponding to the at least one fearing event; placing the audio listening device on the individual's ears; playing the at least one fear-relieving file; and listening to the at least one fear-relieving file to relieve the fear in the individual.

In an embodiment, the at least one fear event can include fear of heights, fear of confined spaces, fear of large places, fear of interacting with other people (social phobia), other fears, or combinations thereof.

In an embodiment, the at least one fear-relieving file comprises: a fear of heights file comprising a plurality of prerecorded phrases comprising one or more of: you are strong, breathe deeply, be brave, rising is not scary but it is your precious opportunity to discover your inner strength, other fear of heights prerecorded phrases, or combinations thereof; a fear of confined spaces file comprising a plurality of prerecorded phrases comprising one or more of: take a deep breath and be calm, close your eyes and imagine a beautiful scene that you love, gently hold your right hand with your left hand and smile, other fear of confined spaces prerecorded phrases, or combination thereof; a fear of large spaces file comprising a plurality of prerecorded phrases comprising one or more of: the vast place holds a lot of beauty and openness, do not let fear prevent you from enjoying it, enjoy the beauty and spaciousness of the place, other fear of large spaces prerecorded phrases, or combinations thereof; and a fear of interacting with other people file comprising a plurality of prerecorded phrases comprising one or more of: take a deep breath and remember that you are no less capable than others, you have many talents and energies that you must share with others, experience the joy of dialogue and sharing conversations with others, life is only sweet by sharing with friends, other fear of interacting with other people prerecorded phrases, or combinations thereof.

In a further embodiment, the audio listening device can include headphones, earbuds, other audio listening devices, or a combination thereof.

In an embodiment, the audio listening device is the headphones.

In an embodiment, the headphones can have a battery compartment, a LCD screen, a memory card slot, a plurality of buttons, a headband, and a plurality of speakers.

In an embodiment, the plurality of buttons can include a play button, a stop/pause button, a skip button, a volume button, and a power button.

In an embodiment, the at least one fear-relieving file can be stored on an insertable memory card and can be configured to be inserted into the memory card slot of the headphones.

In another embodiment, the accessing step can include pressing the skip button on the headphones to select the at least one fear-relieving file displayed on the LCD screen.

In another embodiment, the playing step can include pressing the play button on the headphones.

In another embodiment, the audio listening device is the earbuds.

In another embodiment, the earbuds can be Bluetooth® enabled.

In a further embodiment, at least one Bluetooth® enabled smart mobile device can be configured with an installed fear-relieving mobile app; and wherein the at least one Bluetooth® enabled smart mobile device can be configured to connect to the Bluetooth® enabled earbuds.

In an embodiment, the at least one fear-relieving file can be stored within the fear-relieving mobile app.

In an embodiment, the accessing step can include: opening the fear-relieving mobile app; and selecting the at least one fear-relieving file from a list of fear-relieving files within the fear-relieving mobile app.

In an embodiment, the playing step can include: pressing a play button icon within the fear-relieving mobile app; transferring the plurality of prerecorded phrases corresponding to the selected at least one fear-relieving file from the at least one Bluetooth® enabled smart mobile device to the Bluetooth® enabled earbuds via a Bluetooth® connectivity; and playing the plurality of prerecorded phrases on the Bluetooth® enabled earbuds.

In an embodiment, the plurality of prerecorded phrases can include one or more of: you are strong, breathe deeply, be brave, rising is not scary but it is your precious opportunity to discover your inner strength, other fear of heights prerecorded phrases, or combinations thereof.

In an embodiment, the plurality of prerecorded phrases can include one or more of: take a deep breath and be calm, close your eyes and imagine a beautiful scene that you love, gently hold your right hand with your left hand and smile, other fear of confined spaces prerecorded phrases, or combination thereof.

In another embodiment, the plurality of prerecorded phrases can include one or more of: the vast place holds a lot of beauty and openness, do not let fear prevent you from enjoying it, enjoy the beauty and spaciousness of the place, other fear of large spaces prerecorded phrases, or combinations thereof.

In another embodiment, the plurality of prerecorded phrases can include one or more of: take a deep breath and remember that you are no less capable than others, you have many talents and energies that you must share with others, experience the joy of dialogue and sharing conversations with others, life is only sweet by sharing with friends, other fear of interacting with other people prerecorded phrases, or combinations thereof.

These and other features of the present subject matter will become readily apparent upon further review of the following specification.

BRIEF DESCRIPTION OF DRAWINGS

FIG. 2 depicts a system comprising Bluetooth® enabled earbuds and a Bluetooth® enabled smartphone for relieving fear in an individual.

DETAILED DESCRIPTION

Figure 1:
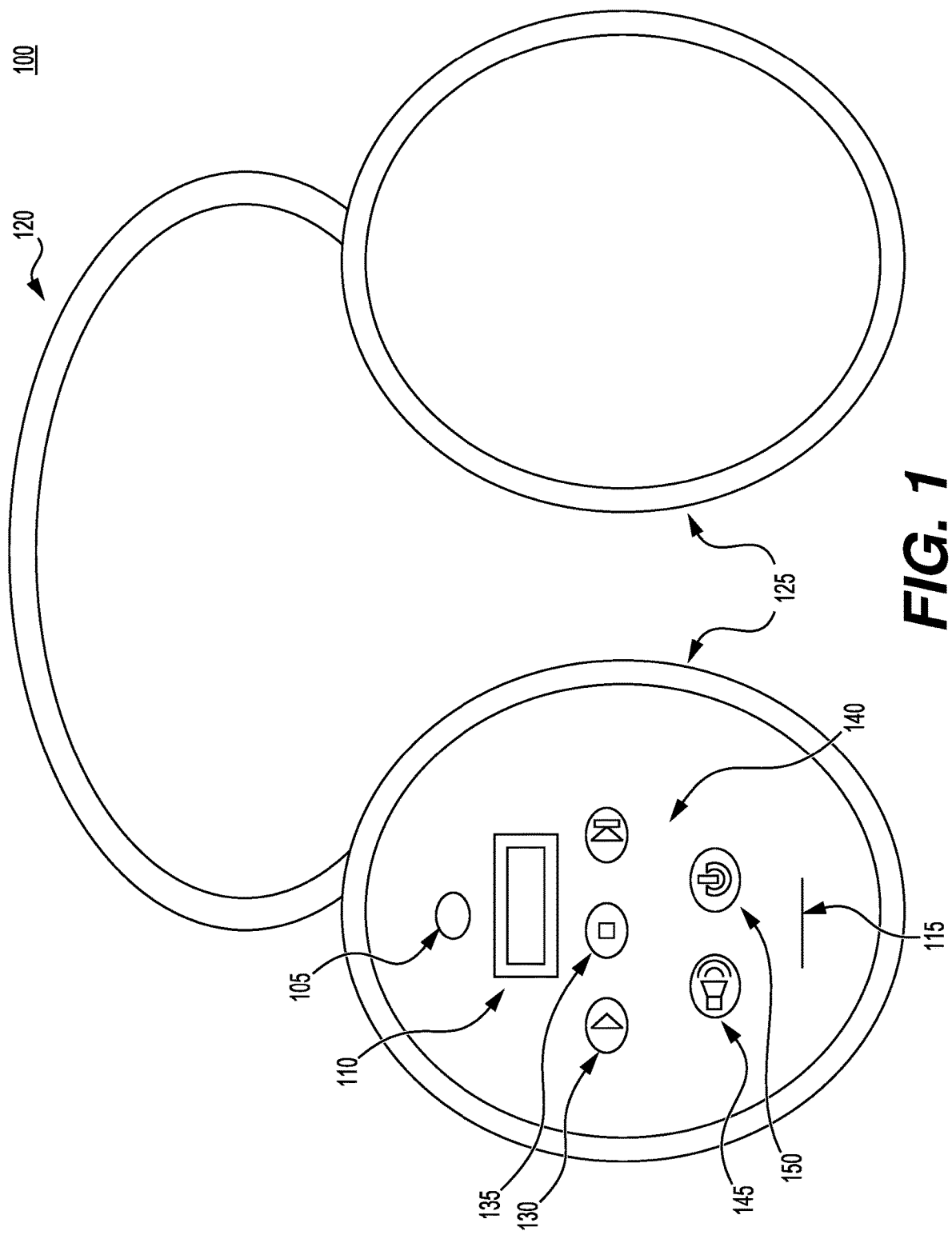
FIG. 1 depicts headphones for relieving fear in an individual.

The following definitions are provided for the purpose of understanding the present subject matter and for construing the appended patent claims. The definitions are not meant to be limiting to the subject matter described herein.

Definitions

Throughout the application, where systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a method of relieving fear in an individual.

In one embodiment, a method of relieving fear in an individual includes experiencing at least one fearing event by the individual; obtaining an audio listening device; accessing at least one fear-relieving file corresponding to the at least one fearing event; placing the audio listening device on the individual's ears; playing the at least one fear-relieving file; and listening to the at least one fear-relieving file to relieve the fear in the individual.

In an embodiment, the at least one fear event can include fear of heights, fear of confined spaces, fear of large places, fear of interacting with other people (social phobia), other fears, or combinations thereof.

In an embodiment, the at least one fear-relieving file comprises: a fear of heights file comprising a plurality of prerecorded phrases comprising one or more of: you are strong, breathe deeply, be brave, rising is not scary but it is your precious opportunity to discover your inner strength, other fear of heights prerecorded phrases, or combinations thereof; a fear of confined spaces file comprising a plurality of prerecorded phrases comprising one or more of: take a deep breath and be calm, close your eyes and imagine a beautiful scene that you love, gently hold your right hand with your left hand and smile, other fear of confined spaces prerecorded phrases, or combination thereof; a fear of large places file comprising a plurality of prerecorded phrases comprising one or more of: the vast place holds a lot of beauty and openness, do not let fear prevent you from enjoying it, enjoy the beauty and spaciousness of the place, other fear of large places prerecorded phrases, or combinations thereof; and a fear of interacting with other people file comprising a plurality of prerecorded phrases comprising one or more of: take a deep breath and remember that you are no less capable than others, you have many talents and energies that you must share with others, experience the joy of dialogue and sharing conversations with others, life is only sweet by sharing with friends, other fear of interacting with other people prerecorded phrases, or combinations thereof.

In a further embodiment, the audio listening device can include headphones (100) as shown in FIG. 1, Bluetooth® enabled earbuds (205) as shown in FIG. 2, other audio listening devices, or a combination thereof.

FIG. 1 depicts, in an embodiment, the headphones (100) which can have a battery compartment (105), a LCD screen (110), a memory card slot (115), a plurality of buttons, a flexible headband (120), and a plurality of speakers (125). The plurality of buttons can include a play button (130), a stop/pause button (135), a skip button (140), a volume button (145), and a power button (150). In a non-limiting embodiment, the headphones (100) can be folded to become a small compact size due to the flexible headband (120).

In an embodiment, the at least one fear-relieving file can be stored on an insertable memory card (not shown) and can be configured to be inserted into the memory card slot (115) of the headphones (100). In certain non-limiting embodiments, other fear-relieving files and/or the individual's prerecorded voices can be stored on the insertable memory card.

In an embodiment, the accessing step can include pressing the skip button (140) on the headphones (100) to select the at least one fear-relieving file displayed on the LCD screen (110). In an embodiment, the playing step can include pressing the play button (130) on the headphones (100).

FIG. 2 depicts, in another non-limiting embodiment, a Bluetooth® enabled system (200) which includes the Bluetooth® enabled earbuds (205), wherein each of the Bluetooth® enabled earbuds (205) have a USB charging port (210). Each of the USB charging ports (210) can be selected from the group consisting of Micro B, Mini B, 8 Pin Lighting, Type A 2.0, Type B 2.0, Type A 3.0, Type B 3.0, Type C 3.0, other USB charging ports, or combinations thereof. The Bluetooth® enabled earbuds (205) can be configured to connect to a Bluetooth® enabled smartphone (215) via Bluetooth® connectivity.

The Bluetooth® enabled smartphone (215) can be configured with an installed fear-relieving mobile app (220). The fear-relieving mobile app (220) can include a play button icon (not shown), a repeat button icon (not shown), a volume control button icon (not shown), a record button icon (not shown), and a stop button icon (not shown). The at least one fear-relieving file can be stored within the fear-relieving mobile app (220). In certain non-limiting embodiments, other fear-relieving files and/or the individual's prerecorded voices can be stored within the fear-relieving mobile app (220).

In an embodiment, the accessing step can include opening the fear-relieving mobile app (220) and selecting the at least one fear-relieving file from a list of fear-relieving files within the fear-relieving mobile app (220). In an embodiment, the playing step can include pressing the play button icon within the fear-relieving mobile app (220); transferring the plurality of prerecorded phrases corresponding to the selected at least one fear-relieving file from the Bluetooth® enabled smartphone (215) to the Bluetooth® enabled earbuds (205) via a Bluetooth® connectivity; and playing the plurality of prerecorded phrases on the Bluetooth® enabled earbuds (205). In certain non-limiting embodiments, the Bluetooth® enabled earbuds (205) can also be configured to connect via Bluetooth® connectivity to other Bluetooth® enabled smart mobile devices, configured with the installed fear-relieving mobile app (220), such as a smart tablet (i.e., Apple iPad, Samsung Galaxy Tab, or other smart tablets) and a smart watch (i.e., Apple Watch, Samsung Galaxy Watch, or other smart watches).

It is to be understood that the method of relieving fear in an individual is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of relieving fear in an individual, the method comprising:
   experiencing at least one fearing event by the individual;
   obtaining an audio listening device;
   accessing at least one fear-relieving file corresponding to the at least one fearing event;
   placing the audio listening device on the individual's ears;
   playing the at least one fear-relieving file; and
   listening to the at least one fear-relieving file to relieve a fear instilled in the individual as a result of the experienced at least one fearing event,
   wherein the at least one fearing event comprises fear of heights, fear of confined spaces, fear of large places, fear of interacting with other people, or combinations thereof, and
   wherein the at least one fear-relieving file comprises:
   a fear of heights file comprising a plurality of prerecorded phrases, said plurality of prerecorded phrases comprising one or more of:
   you are strong,
   breathe deeply,
   be brave,
   rising is not scary but it is your precious opportunity to discover your inner strength, other fear of heights prerecorded phrases,
   or combinations thereof;
   a fear of confined spaces file comprising a plurality of prerecorded phrases, said plurality of prerecorded phrases comprising one or more of:
   take a deep breath and be calm,
   close your eyes and imagine a beautiful scene that you love,
   gently hold your right hand with your left hand and smile,
   other fear of confined spaces prerecorded phrases,
   or combination thereof;
   a fear of large places file comprising a plurality of prerecorded phrases, said plurality of prerecorded phrases comprising one or more of:
   the vast place holds a lot of beauty and openness,
   do not let fear prevent you from enjoying it,
   enjoy the beauty and spaciousness of the place,
   other fear of large places prerecorded phrases,
   or combinations thereof; and a fear of interacting with other people file comprising a plurality of prerecorded phrases, said plurality of prerecorded phrases comprising one or more of:
take a deep breath and remember that you are no less capable than others,
you have many talents and energies that you must share with others,
experience the joy of dialogue and sharing conversations with others,
life is only sweet by sharing with friends,
other fear of interacting with other people prerecorded phrases,
or combinations thereof.

2. The method of claim 1, wherein the audio listening device comprises headphones, earbuds, other audio listening devices, or a combination thereof.

3. The method of claim 2, wherein the audio listening device is the headphones.

4. The method of claim 3, wherein the headphones comprise a battery compartment, a LCD screen, a memory card slot, a plurality of buttons, a headband, and a plurality of speakers.

5. The method of claim 4, wherein the plurality of buttons comprise a play button, a stop/pause button, a skip button, a volume button, and a power button.

6. The method of claim 5, wherein the at least one fear-relieving file is stored on an insertable memory card configured to be inserted into the memory card slot of the headphones.

7. The method of claim 6, wherein the accessing step comprises pressing the skip button on the headphones to select the at least one fear-relieving file displayed on the LCD screen.

8. The method of claim 7, wherein the playing step comprises pressing the play button on the headphones.

9. The method of claim 2, wherein the audio listening device is the earbuds.

10. The method of claim 9, wherein the earbuds include a first transceiver configured to exchange wireless data between electronic devices over a short range.

11. The method of claim 10, further comprising at least one smart mobile device configured with an installed fear-relieving mobile app; wherein the at least one smart mobile device includes a second transceiver configured to exchange wireless data between electronic devices over a short range, the second transceiver being configured to be communicatively coupled with the first transceiver to wirelessly connect the earbuds to the at least one smart mobile device.

12. The method of claim 11, wherein the at least one fear-relieving file is stored within the fear-relieving mobile app.

13. The method of claim 12, wherein the accessing step comprises:
opening the fear-relieving mobile app; and
selecting the at least one fear-relieving file from a list of fear-relieving files within the fear-relieving mobile app.

14. The method of claim 13, wherein the playing step comprises:
pressing a play button icon within the fear-relieving mobile app;
wirelessly transferring the plurality of prerecorded phrases corresponding to the selected at least one fear-relieving file from the at least one smart mobile device to the earbuds via the first and second transceivers; and
playing the plurality of prerecorded phrases on the earbuds.

* * * * *